US006308721B1

(12) United States Patent
Bock et al.

(10) Patent No.: US 6,308,721 B1
(45) Date of Patent: Oct. 30, 2001

(54) CARTRIDGE HOLDER FOR A DIALYSER

(75) Inventors: Gerhard Bock, Friedewald; Reinhold Otto, Mosheim; Robert Mardorf, Melsungen, all of (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 09/432,226

(22) Filed: Nov. 3, 1999

(30) Foreign Application Priority Data

Nov. 17, 1998 (DE) .............................................. 198 52 982

(51) Int. Cl.⁷ ...................................................... B08B 9/027
(52) U.S. Cl. ........................................ 134/166 R; 422/300
(58) Field of Search ........................... 134/166 R, 166 C, 134/169 R, 169 C; 422/300

(56) References Cited

FOREIGN PATENT DOCUMENTS

0278100   12/1987  (EP) .
WO/97/
020506    7/1996   (WO) .

*Primary Examiner*—Philip R. Coe
(74) *Attorney, Agent, or Firm*—Diller, Ramik & Wight

(57) ABSTRACT

The cartridge holder comprises a lower jaw with a drain connector and an upper jaw with a supply connector. A cartridge may be placed between both jaws, the nipples of the cartridge being connected with the connectors. For flushing or disinfecting, the upper jaw is lowered to the lower jaw. An intermediate jaw, previously swivelled to the side, is automatically aligned with the lower jaw so that it interconnects the connectors of the outer jaws. The connectors of the outer jaws are alike. The intermediate jaw is provided with connection elements fitting into the connectors. Thus, it acts as an adapter.

8 Claims, 8 Drawing Sheets

CARTRIDGE HOLDER FOR A DIALYSER

BACKGROUND OF THE INVENTION

The present invention relates to a cartridge holder for a dialyser in which the hemodialysis solution is prepared by dissolving a salt contained in a cartridge or by diluting a liquid concentrate.

In dialysers, a hemodialysis solution is prepared and passed through a dialyser to extract contaminants from a patient's blood. Moreover, the dialyser is disinfected prior to a treatment. From EP 0 278 100 B1, it is known to produce the hemodialysis solution by dissolving a powder in water within the dialyser by flowing water through a cartridge containing the powder. Generally, the powder is sodium bicarbonate. Thus, a liquid concentrate is prepared that will later be diluted with water to obtain the concentration required for hemodialysis.

WO 97/02056 describes a cartridge holder for a dialyser wherein the cartridge is inserted between two jaws adapted for relative displacement along a linear guide. When inserting the cartridge between the jaws, thorns on the jaws penetrate into the cartridge and connections, also provided on the jaws, make the fluid communication with the interior of the cartridge. Thus, water may be supplied through the upper jaw, whereas the salt-water solution is drained from the lower jaw. For desalting, cleaning or disinfecting, it is required to flush the liquid leading parts of the cartridge holder. To do this, the connections of the jaws may be abutted directly against each other so that they form a conduit through which a flushing or disinfection liquid is passed. In doing so, the liquid conducting parts and also the seals are rinsed. To make the short circuit possible, both jaws are of a complicated structure with various sealing elements. The connections of both jaws are basically of the same connection type, i.e. they have a recess for a sealed insertion of a projection of the cartridge, as well as a thorn. As a consequence, the connections of the upper and the lower jaw do not fit together directly. Therefore, these connections have to be modified by embracing additional connection elements such that they may be abutted in a sealing manner. Thereby, the structure of the two connections become complicated.

It is an object of the present invention to provide a cartridge holder that allows for a connection or a short-circuiting of the two jaws without these jaws having to be modified.

SUMMARY OF THE INVENTION

The present cartridge holder is provided with an intermediate jaw or adapter that may be inserted between the lower and the upper jaw to join the connections of these jaws. It is an essential advantage that the connections of the lower and the upper jaw may be alike since they are not plugged together directly. On the intermediate jaw, the corresponding counter-connection elements matching the respective connection on the lower and the upper jaw. Thus, those connections that are for the connection with the cartridge, may also be used for connection with the intermediate jaw so that no additional sealing elements are required that would be subjected to salt deposition or encrustation. The counter-connection elements of the intermediate jaw are easy to clean and to disinfect, since they are readily accessible when the intermediate jaw is inactive.

In a preferred embodiment of the present invention, the intermediate jaw may be pivoted about an axis extending parallel to the displacement direction of the upper and the lower jaw. The intermediate jaw is displaced along the same bar along which also the upper or the lower jaw is displaced. Further, it may be pivoted about this bar. The intermediate jaw is an integral part of the vertical guiding on which the movable jaw slides. It may be pivoted about the axis of this guiding.

Preferably, the intermediate jaw is pivoted about a vertical axis, said pivoting being controlled by the vertical position of the upper jaw, the intermediate jaw then moving into the plane of the two outer jaws, when the upper jaw sinks beneath a minimum height. This minimum height is lower than the vertical position taken by the upper jaw with the cartridge inserted. When the upper jaw is below this minimum height, the intermediate jaw is automatically pivoted into the plane of the two outer jaws so that the outer jaws cannot contact each other, because the intermediate jaw moves in before. This control of the intermediate jaw may be effected by sequential control, link motion control or cam control.

It is generally possible to manually displace the movable jaw, usually the upper jaw, along the guide rail. By manually displacing the upper jaw, the force for pivoting the intermediate jaw is applied as well. According to another solution, the displaceable jaw is displaced automatically using a spindle or another power transmission device. Here, the upper jaw is moved under automatic control and/or by manually actuating a switch. The pivot movement of the intermediate jaw is preferably controlled by the movable jaw through a cam control.

The intermediate jaw is moved such that it is lowered onto the lower jaw after having been pivoted into the plane of the outer jaws. Thereby, it is possible to make the connection element of the intermediate jaw engage the connection of the lower jaw in mutual alignment. When they are moved apart subsequently, the intermediate jaw is first lifted linearly and is pivoted only after its connection element has been separated from the connection of the lower jaw.

It is possible to merely use the intermediate jaw as an adapter interconnecting the similar connections of the two outer jaws, when there is no cartridge between them. On the other hand, it is also possible to use the intermediate jaw for disinfecting the holder in the liquid conduit. Further, the intermediate jaw may include a tank containing the disinfectant in the form of a soluble powder or concentrate. During disinfection, the powder is dissolved in the existing liquid path using water and it is then introduced in a diluted form into the liquid paths of the dialyser for disinfection. The disinfectant may also be contained in the intermediate jaw as a liquid concentrate diluted with water in the liquid path. Thus, the intermediate jaw may have a tank containing the flushing or disinfecting agent as a soluble powder. In this case, water must merely be supplied to obtain a solution in the form of a concentrate, necessary for the treatment of the device. The size of the intermediate jaw may correspond to the size of the cartridges used to prepare the hemodialysis solution.

In a particularly suitable embodiment of the invention, the intermediate jaw comprises a cartridge support and is pivotable such that, in one position, the connection elements and, in the other position, the cartridge support are aligned with the connections of the lower and the upper jaw. Here, the cartridge support may be pivoted into an inactive position when being flushed and be provided with a new cartridge. After the end of the flushing, the cartridge support with the new cartridge is automatically swivelled into the service position. When the powder supply contained in a cartridge is used up, this cartridge may be pivoted out of alignment with the two jaws so that the water may be drained therefrom outside the service position. Further, it is possible to automatically eject the cartridge and supply new ones.

DESCRIPTION OF THE DRAWINGS

The following is a detailed description of embodiments of the invention taken in conjunction with the drawings.

In the Figures:

FIG. 6 is a view in the direction of the arrows VI—VI in FIG. 5, FIG. 7 a section along line VII—VII of FIG. 5.

DETAILED DESCRIPTION OF PREFERRED EMBODIMENTS

Figure 1:
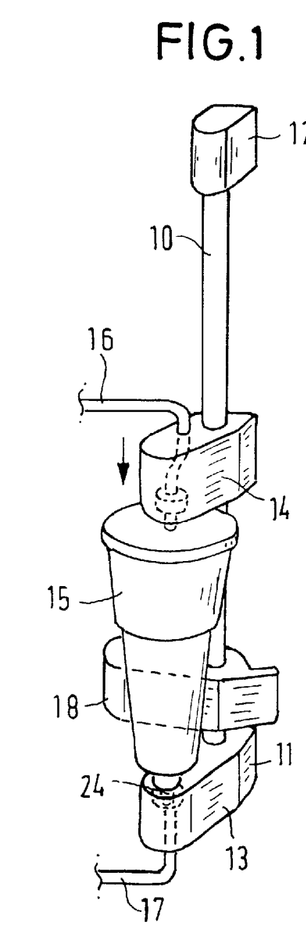
FIG. 1 is a perspective view of the cartridge holder in the service position with a cartridge installed.

In the embodiment of FIGS. 1–10, a vertical guide rod 10 is provided that may be mounted on the front side of a dialyser (not illustrated). The guide rod 10 has a holder 11 at its lower end and a holder 12 at its upper end, which are both fastened at the dialyser. Fastened to the lower holder 11 is the lower jaw 13 in the shape of a forward slanted projecting arm. An upper jaw 14 may be moved along the guide rod 10. The upperjaw 14 is non-rotatably guided on the guide rod and it is congruent with the lower jaw 13. As illustrated in FIG. 1, a cartridge 15, containing a powder of bicarbonate concentrate, may be set on the lower jaw 13, whereupon the upper jaw 14 is pushed down to cooperate with the upper portion of the cartridge 15. A supply line 16 leads into the upper jaw 14 and a drain line 17 leads from the lower jaw 13.

Between the two jaws 13, 14, an intermediate jaw 18 is arranged which is also guided on the guide rod 10. In contrast to the upper jaw 14, however, the intermediate jaw 18 may be pivoted about the guide rod 10.

Each of the jaws 13 and 14 comprises a fluid connection 19, 20, respectively. Each fluid connection comprises a socket portion 21 (FIG. 5) with a central indentation 22 and a thorn 23 projecting from the bottom of the indentation. The cartridge 15 has a cylindric nipple 24 at its lower end and an cylindric nipple 25 at its upper end. The nipple 24 is mated with the indentation 22, the thorn 23 penetrating the end wall of the nipple 24, establishing the connection between the drain line 17 and the interior of the cartridge. Similarly, the upper nipple 25 is introduced in a sealing manner into the indentation 22 of the upper connection 20, the thorn 23 penetrating the end wall of the nipple 25, establishing the connection between the interior of the cartridge and the supply line 16.

After the cartridge 15 of FIG. 1 has been set up on the lower jaw 13, with the nipple 24 received in the indentation 22 of the connection 19 in a sealing manner, the upper jaw 14 is shifted downward towards the cartridge until the thorn of the connection 20 penetrates the cartridge wall. The jaws 13, 14 securely hold the cartridges in a vertical state and water is supplied via the supply line 16, in which the salt contained in the cartridge 15 is dissolved. The supply line 16 includes a shut-off valve that opens in dependence on the position of the intermediate jaw 18 and the upper jaw 14 as determined by sensors. The solution is bled off via the line 17.

Figure 2:
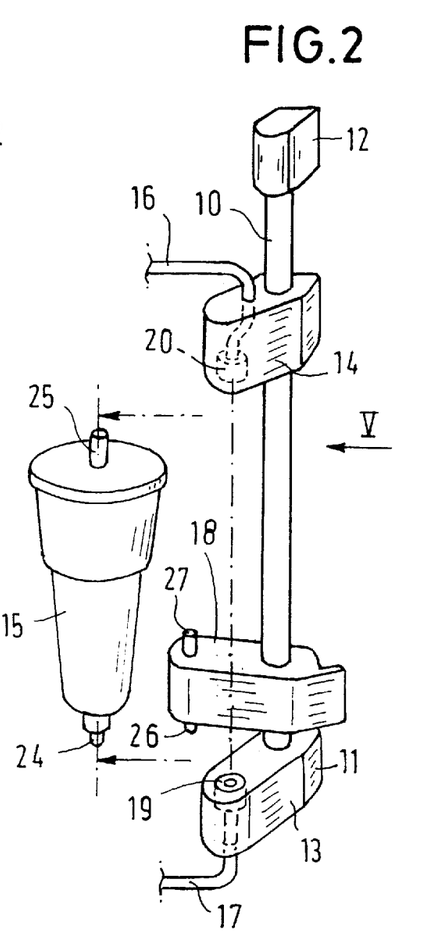
FIG. 2 illustrates a change of cartridges.

FIG. 2 illustrates the removal of the cartridge 15. The upper jaw 14 is pushed up so that the cartridge 15 is cleared and may be removed laterally after slightly lifting the same.

Figure 3:
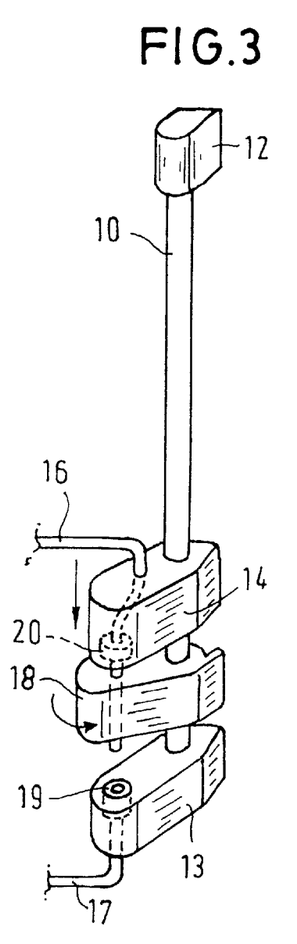
FIG. 3 shows the lowering of the upper jaw and the pivoting of the intermediate jaw.
Figure 4:
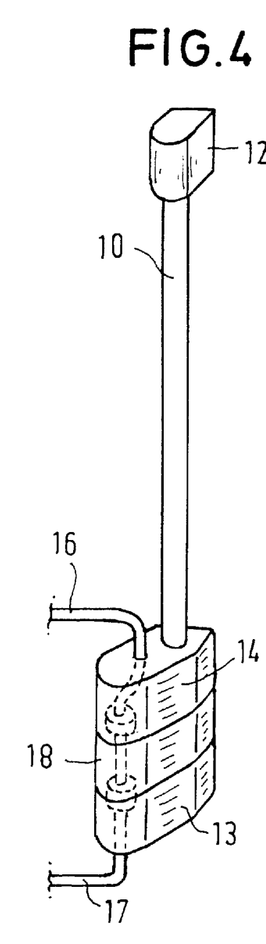
FIG. 4 illustrates the three jaws in the connected state during flushing or disinfection.

To disinfect and flush the line system of the cartridge holder, the upper jaw 14 is shifted downward from the position illustrated in FIG. 2, as is shown in FIG. 3. Here, the intermediate jaw 18 is automatically pivoted from the standby position of FIG. 2 into the service position. The pivoting is done automatically using a dog as soon as the vertical position of the upper jaw 14 drops beneath a predetermined minimum vertical position that is lower than the service position illustrated in FIG. 1. The force of the downward movement of the upper jaw 14 causes the intermediate jaw 18 to be pivoted such that it is aligned with the outer jaws 13, 14. This alignment will be achieved before the three jaws contact each other. Thereafter, pushing down the upper jaw 14 further causes the intermediate jaw 18 to be connected with the outer jaws 13 and 14. When the intermediate jaw 18, as illustrated in FIG. 4, is aligned with the outer jaws 13, 14 and has its connection elements 26, 27 inserted into the connections 19, 20 in a sealing manner, the supply line 16 and the drain line 17 are short-circuited, and the line system thus formed may be flushed with a rinsing and/or disinfecting agent. The alignment of the intermediate jaw 18, as illustrated in FIG. 4, is detected by a sensor in the lower jaw, so as to initiate a flushing only when the jaws are in proper alignment.

After flushing, the upper jaw 14 is pushed up with the intermediate jaw 18 first being lifted in parallel and then being pivoted outward about the guide rod 10. Upon reaching the position illustrated in FIG. 2, a new cartridge 15 may be inserted and fixed by pressing down the upper jaw 14.

The pivoting of the intermediate jaw 18 is controlled by a cam 28 mounted on an arm 29 extending downward from the upper jaw 14. The vertical length of the arm 29 exceeds the height of the intermediate jaw 18.

The cam 28 cooperates with a guide groove 30 provided in a cylindric portion 31 on the rear of the intermediate jaw 18. The intermediate jaw 18 may be moved vertically within limits, namely from the abutting position illustrated in FIGS. 4 and 9 into the lifting position illustrated in FIGS. 3 and 8, where the projecting lower connection element 26 just gets clear of the lower jaw 13. The abutting position may be taken only when the intermediate jaw 18 is in exact alignment with the lower jaw 13.

Figure 5:
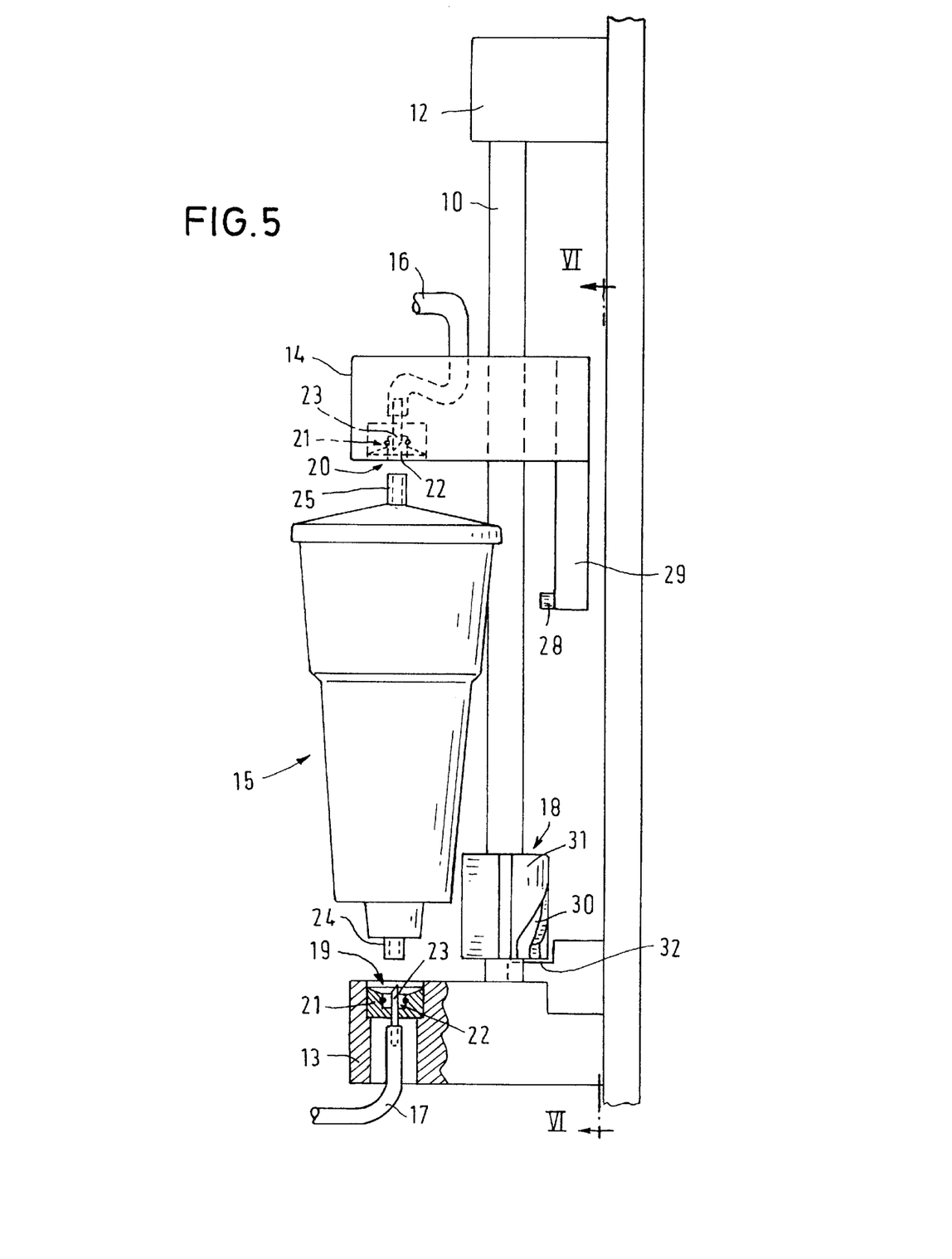
FIG. 5 is a view on FIG. 2 in the direction of the arrow V.
Figures 6, 7:
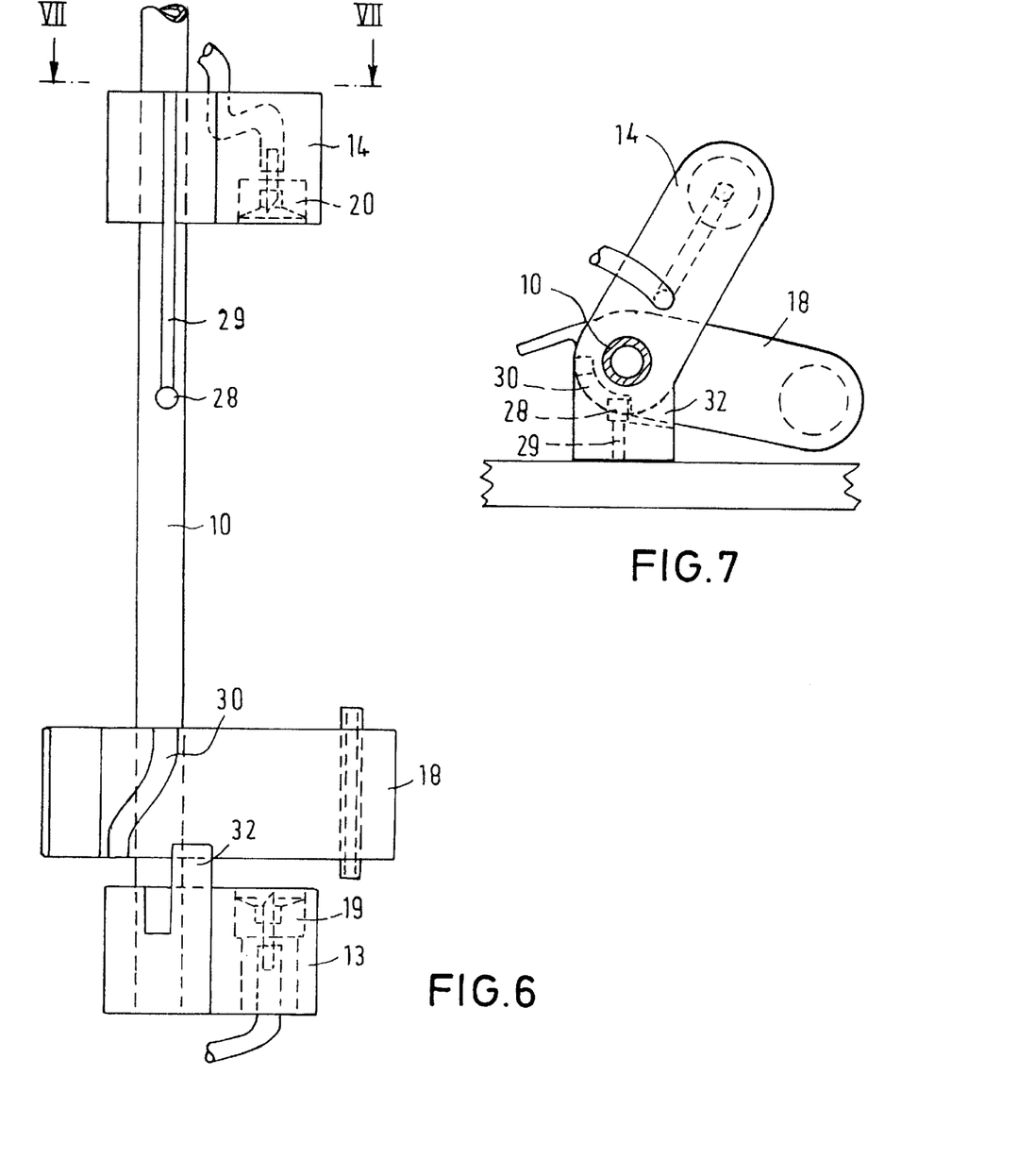
Figure 8:
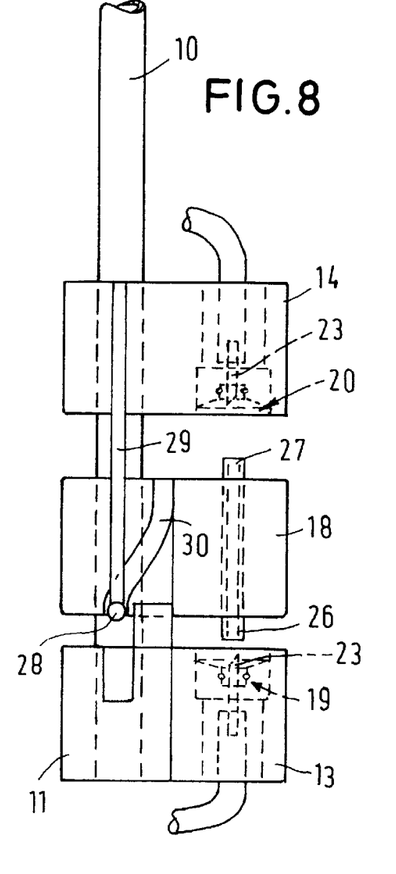
FIG. 8 is a representation similar to FIG. 6, showing the state of lowering the upper jaw and pivoting the intermediate jaw.
Figure 9:
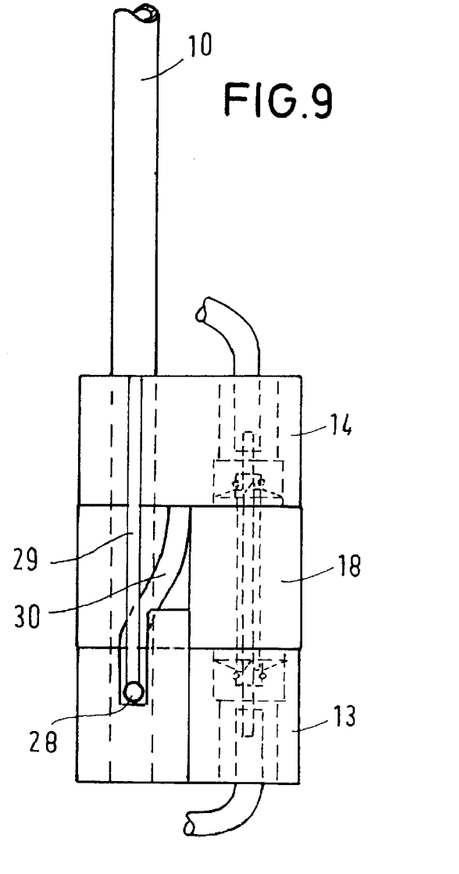
FIG. 9 is a representation similar to FIG. 8, showing all three jaws in an interconnected state.
Figure 10:
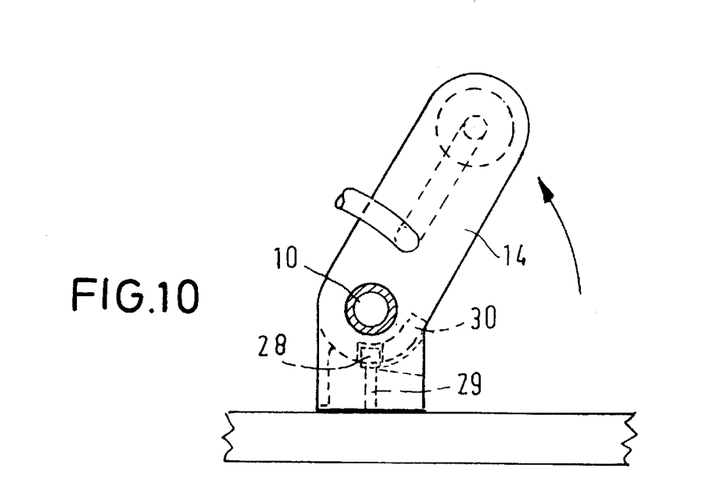
FIG. 10 is a representation similar to FIG. 7, showing the aligned state of all three jaws of FIG. 9.

Upon lowering the upper jaw 14, the cam 28 engages the upper end of the guide groove 30 of the outward pivoted intermediate jaw 18 when the minimum vertical position is exceeded (see FIGS. 5 and 6). The guide groove 30 has a beveled flank so that the intermediate jaw 18 is pivoted about the axis of the guide rail 10 when the cam 30 is moved vertically downward through the guide groove 30.

In the lifted position and pivoted outward, the intermediate jaw 18 rests on an abutment surface 32 of the holder 11. The intermediate jaw can sink from the lifted position only, if it has previously been aligned with the outer jaws 13, 14. In the course of its downward movement, the upper jaw first pivots the intermediate jaw 18 to the side by the cam 28 engaging the guide groove 30, and afterwards, the intermediate jaw 18 sinks onto the lower jaw 13 by its own weight, the connection element 26 penetrating into the connector 19. When the upper jaw 14 is pressed further down, it fully abuts the intermediate jaw 18, the connection element 27 thereof entering the connector 20.

The connectors 19 and 20 are designed alike. In the present case, they are female connectors, whereas the connection elements 26, 27 of the intermediate jaw 18 are male.

When pulling the upper jaw 14 up, it will first separate from the intermediate jaw 18. Then, it will take the intermediate jaw 18 along for a short vertical upward distance and, finally, it will pivot the intermediate jaw 18 by the effect of the cam 28 engaging the beveled portion of the guide groove 29.

Different from the embodiment described, the device may also be motor-operated, with the upper jaw 14 being driven vertically by a spindle, for example.

A modified solution employing a motor is described in FIGS. 11–19. Here, the lower jaw 13 is also immovably fixed to a guide rail 10, while the upper jaw 14 may be displaced along the guide rail 10 and is secured against pivoting. A spindle extends in the guide rail 10, the spindle being driven by a motor 35. The motor 35 comprises a position sensor 36 providing information on the spindle position. A spindle screw sits on the spindle, being fastened within the upper jaw 14. Thus, the drive motor 35 displaces the upper jaw 14 vertically, the position sensor 36 providing information on the vertical position.

The intermediate jaw 18 further comprises a cartridge support 37. This is a ring into which the cartridge 15 is placed such that its lower end protrudes therefrom. The cartridge support 37 is mounted laterally to the intermediate jaw 18 so that it will not interfere with the lowering of the upper jaw 14 onto the intermediate jaw 18 even with the cartridge 15 installed.

Figure 11:
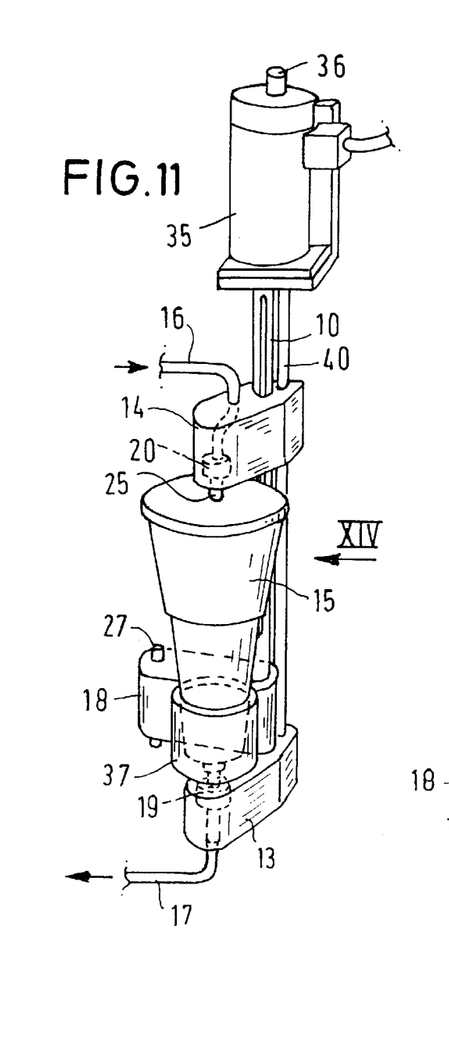
FIG. 11 illustrates a second embodiment of the cartridge holder with a cartridge installed and held by a cartridge support.
Figure 12:
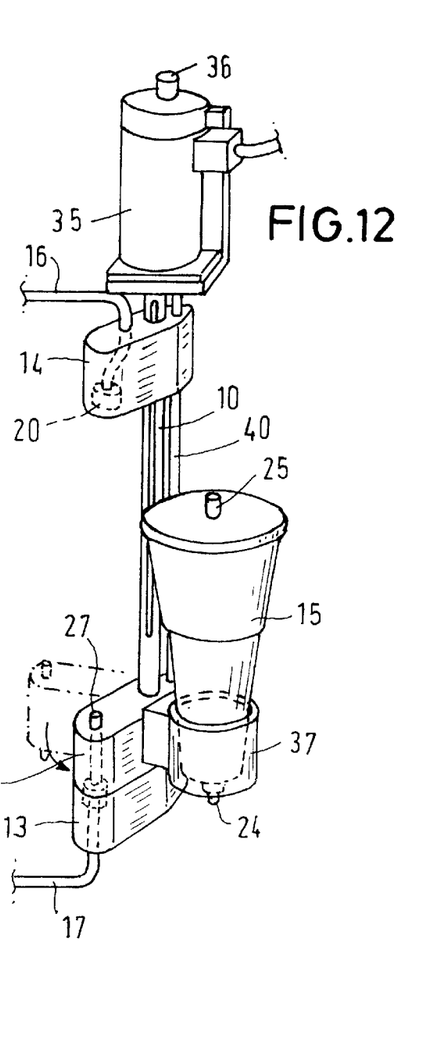
FIG. 12 shows the pivoting of the intermediate jaw and the simultaneous pivoting of the cartridge support.

In FIG. 11, the intermediate jaw 18 is pivoted to the side so that the cartridge support 37 is centered over the connector 24 of the lower jaw 13. The lower nipple of the cartridge 15 is inserted into the connector 19 and the upper nipple is inserted into the connector 20. This is the service position.

Figure 13:
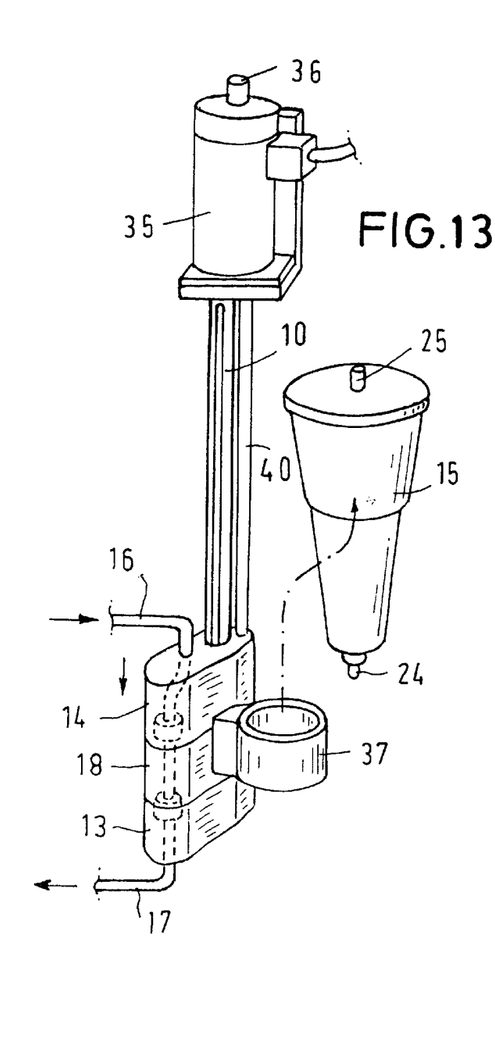
FIG. 13 illustrates the flushing state with the change of cartridge.

For flushing, the motor 35 is first driven such that it lifts the upper jaw 14. After having passed a predetermined position, the intermediate jaw 18 is taken along, so that it lifts the cartridge support 37 and the cartridge comes clear of the lower jaw 13. When the upper jaw 14 is moved up further, the intermediate jaw 18 is pivoted into the aligned position depicted in FIG. 12, the cartridge support 37 assuming a lateral position. After the highest position of the upper jaw 14 has been reached, the motor 35 is reversed so that it drives in the opposite direction and lowers the jaw 14. During lowering, the jaw 14 presses on the intermediate jaw 18, with all three jaws being aligned and in fluid communication, as illustrated in FIG. 13. In this state, the flushing or disinfecting may be effected. While this happens, the cartridge 15 may be taken from the cartridge support 37 and replaced. After the flushing is finished, the jaw 14 is moved up, whereby, after a short upward travel, it pivots the intermediate jaw 18 and moves the cartridge support 37 into alignment with the two outer jaws 13 and 14. Thereafter, the upper jaw 14 is lowered to press the nipples 24, 25 of the cartridge into the respective seat of the connector of the jaw 13 or 14. The entire motion sequence is controlled by the position signals provided by the position sensor 36.

Figure 14:
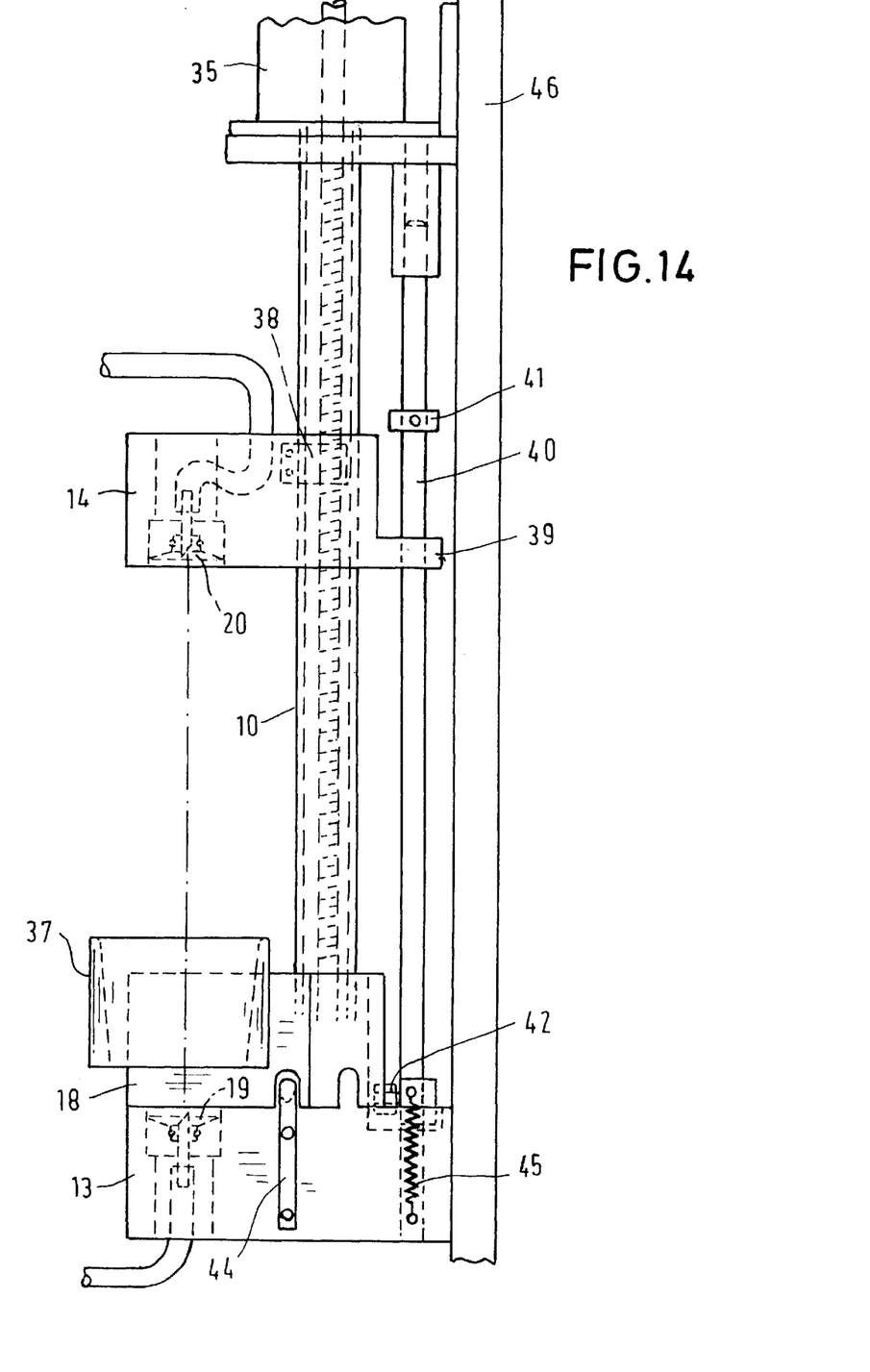
FIG. 14 is a view on FIG. 11 in the direction of the arrow XIV.

FIG. 14 illustrates a guide rail 10 in the shape of a hollow tube with a longitudinal slit at the front side, through which projects a projection of a spindle nut 38. The spindle nut provided inside the guide rail 10 is fastened at the upperjaw 14 so that the motor 35 controls the vertical positioning of the jaw 14. The jaw 14 has a projection 39 on the rear end through which a control rod 40 extends. The rod is provided with a dogging ring 41. When the jaw 14 moves up, it takes along the control rod 40 by the dogging ring 41 and the rod controls the pivot movement of the intermediate jaw 18 via a cam 42. A spring 45 pulls the control rod 40 down. A guide pin 44 at the lower jaw 13 makes sure that the intermediate jaw 18 can be lowered onto the lowerjaw 13 only when in exact alignment therewith and it also guarantees this alignment during lifting.

Figures 15, 16, 17:
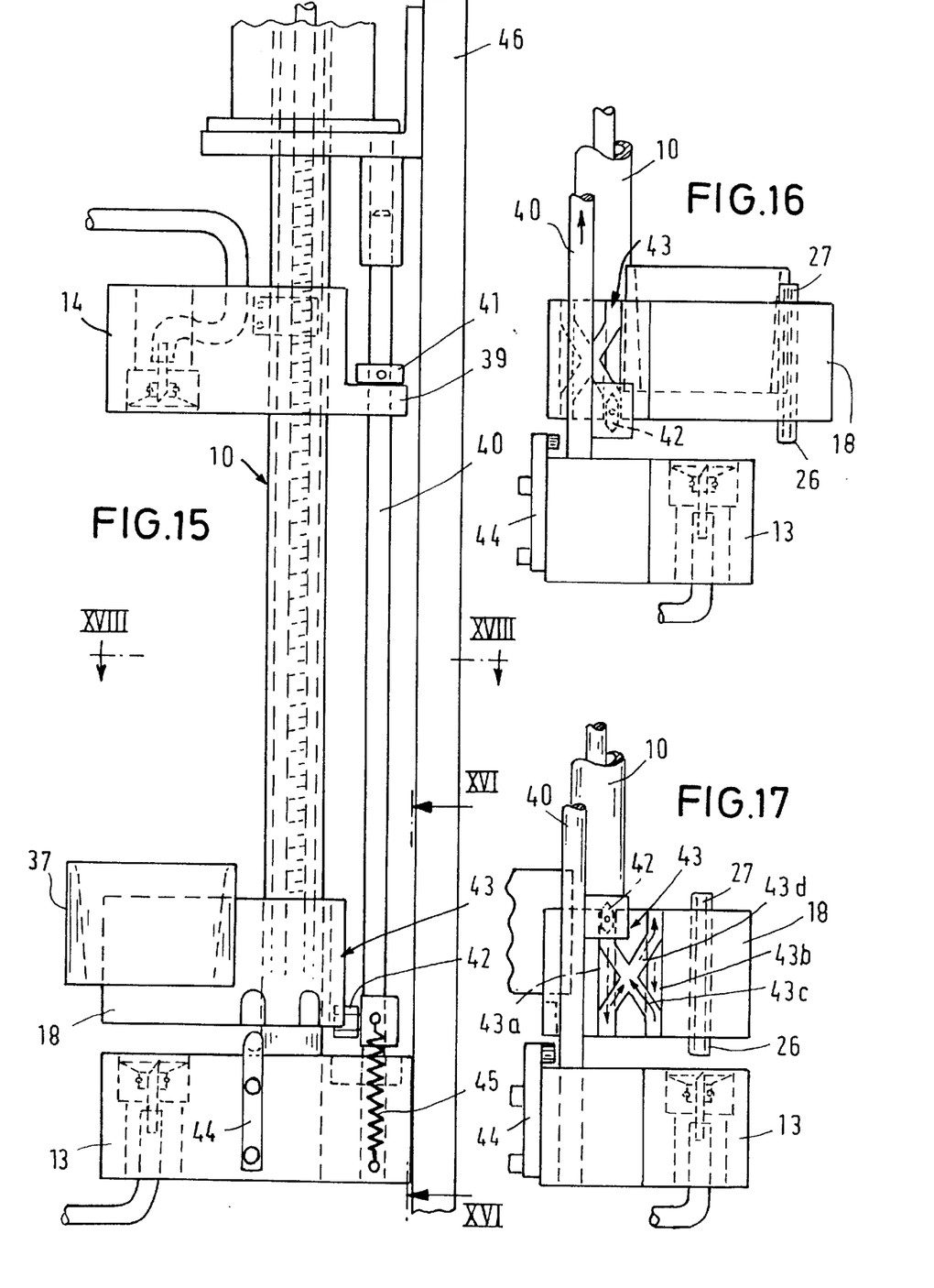
FIG. 15 is a representation similar to FIG. 14, showing the lifting of the upper jaw.
FIG. 16 is a section along line XVI—XVI in FIG. 15.
FIG. 17 is a representation similar to FIG. 16, showing the pivoting of the intermediate jaw.
Figure 18:
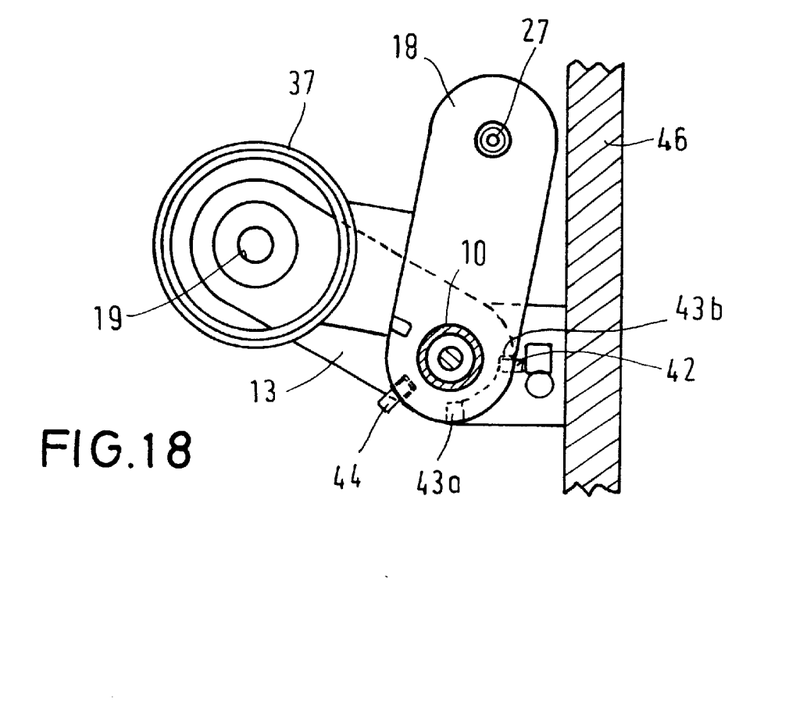
FIG. 18 is a section along line XVIII—XVIII in FIG. 15.
Figure 19:
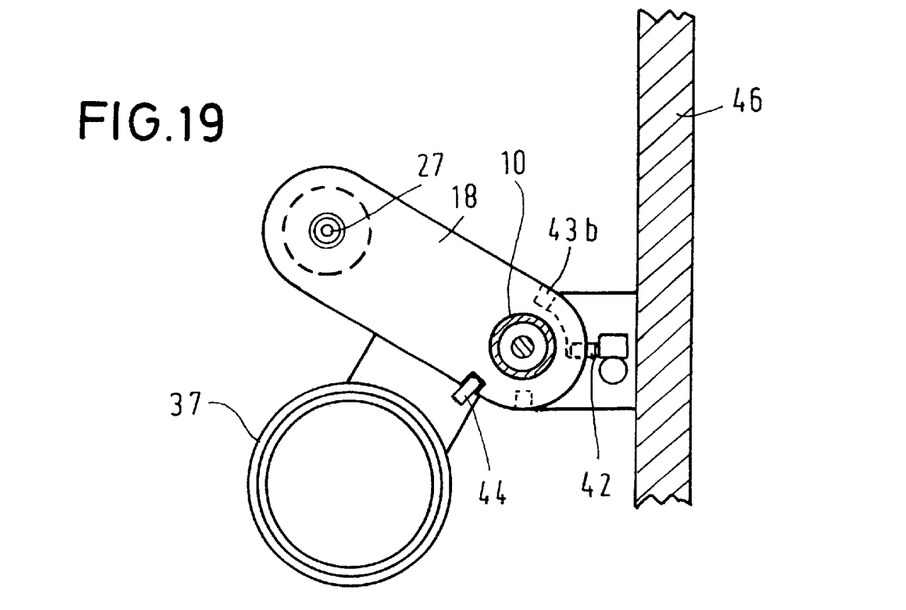
FIG. 19 is a representation similar to FIG. 18, showing the position of the intermediate jaw during flushing.

The cam 42 engages guide grooves 43 of the intermediate jaw 18, depicted in FIGS. 16 and 17. These are two vertical guide grooves 43a, 43b and two diagonal guide grooves 43c, 43d connecting the vertical guide grooves. When the control rod 40 moves down, the cam 42 first travels down in the vertical guide groove 43a. In the lowermost end position, the cam 42 is slightly tilted, so that, when moving up subsequently, it travels in the diagonal guide groove 43d, pivoting the intermediate jaw 18 outward. When the cam 42 is moved down again, it moves down into the guide groove 43b, whereby the cartridge support 37 is lowered and the cartridge is positioned. When moving the cam 42 up again, the cam will travel into the diagonal guide groove 43c, whereby the intermediate jaw 18 is first lifted and the again aligned with the two outer jaws 13, 14.

The wall to which the cartridge holder is fastened is given the reference numeral 46. This may be, for example, the front wall of the dialyser.

What is claimed is:

1. A cartridge holder for a dialyser, comprising a lower jaw and an upper jaw, each with connectors for a cartridge and being movable with respect to each other to assume a first position in which the jaws receive the cartridge between them, and a second position in which the jaws are short-circuited for flushing or disinfection, and comprising an intermediate jaw adapted to be inserted between the upper and the lower jaws to interconnect the connectors of these jaws.

2. The cartridge holder of claim 1, wherein the intermediate jaw may be pivoted about an axis extending in parallel to the direction of displacement of the upper or lower jaw.

3. The cartridge holder of claim 1, wherein the intermediate jaw is pivotable about a vertical axis, depending on the vertical position of the upper jaw, whereby the intermediate jaw moves into the plane of the two outer jaws when the upper jaw is lowered below a minimum vertical position.

4. The cartridge holder of claim 1, wherein the intermediate jaw is controlled such that after having pivoted into the plane of the two outer jaws, it is lowered onto the lower jaw.

5. The cartridge holder of claim 1, wherein the intermediate jaw has its bottom and top faces provided with similar connection elements for connection with the connectors of the lower and upper jaws, which are also similar.

6. The cartridge holder of claim 1, wherein the intermediate jaw comprises a tank for holding a flushing or disinfecting agent.

7. The cartridge holder of claim 1, wherein the intermediate jaw comprises a cartridge support and is pivotable such that, in the one position, the connection elements and, in the other position, the cartridge support is aligned with the connectors of the lower and upper jaws.

8. The cartridge holder of claim 7, wherein in the short-circuit position and in the service position, the intermediate jaw is lowered towards the lower jaw without pivoting.

* * * * *